United States Patent [19]

Lloyd et al.

[11] 4,209,585

[45] Jun. 24, 1980

[54] METHOD AND APPARATUS FOR THE AUTOMATIC MICROBIOLOGICAL SAMPLING OF A LIQUID PRODUCT

[76] Inventors: Harold L. Lloyd, 10654 Pioneer Ave., Oakdale, Calif. 95361; Richard A. Branscombe, 1629 Sheldon Dr.; Robert C. Oliver, 2409 Cheryl La., both of Modesto, Calif. 95350

[21] Appl. No.: 924,545

[22] Filed: Jul. 14, 1978

[51] Int. Cl.$^2$ .................. C12Q 1/24; C12Q 1/04; C12M 1/36; C12M 1/26
[52] U.S. Cl. ........................... 435/30; 435/31; 435/34; 435/287; 435/289; 435/291; 435/292; 435/296; 435/311; 435/316; 435/803
[58] Field of Search ............... 195/103.5 M, 103.5 R, 195/127, 139; 422/62; 435/29, 30, 31, 32, 33, 34, 287, 289, 291, 292, 296, 299, 300, 301, 311, 316, 803, 813

[56] References Cited

U.S. PATENT DOCUMENTS

| | | | |
|---|---|---|---|
| 3,772,154 | 11/1973 | Isenberg et al. | 195/127 X |
| 3,902,971 | 9/1975 | Fletcher et al. | 195/103.5 R |
| 3,926,738 | 12/1975 | Nyiri et al | 195/127 |

*Primary Examiner*—Robert J. Warden
*Attorney, Agent, or Firm*—Townsend and Townsend

[57] ABSTRACT

A method and apparatus for the automatic sampling for microorganisms in a liquid product flowing in a processing line. A stream of the product is directed away from the processing line and automatically injected in sequence into a plurality of microorganism collection devices. The stream is injected into each of the collection devices for a predetermined time interval. The collection devices contain sterile membranes which filter microorganisms out of the stream. Subsequent incubation of the membranes on nutrient media permits growth and detection of microorganism colonies. The detection of microorganism colonies in one of the collection devices permits the isolation of suspect liquid product bottled during the time interval when the collection device filtered microorganisms from the stream.

32 Claims, 3 Drawing Figures

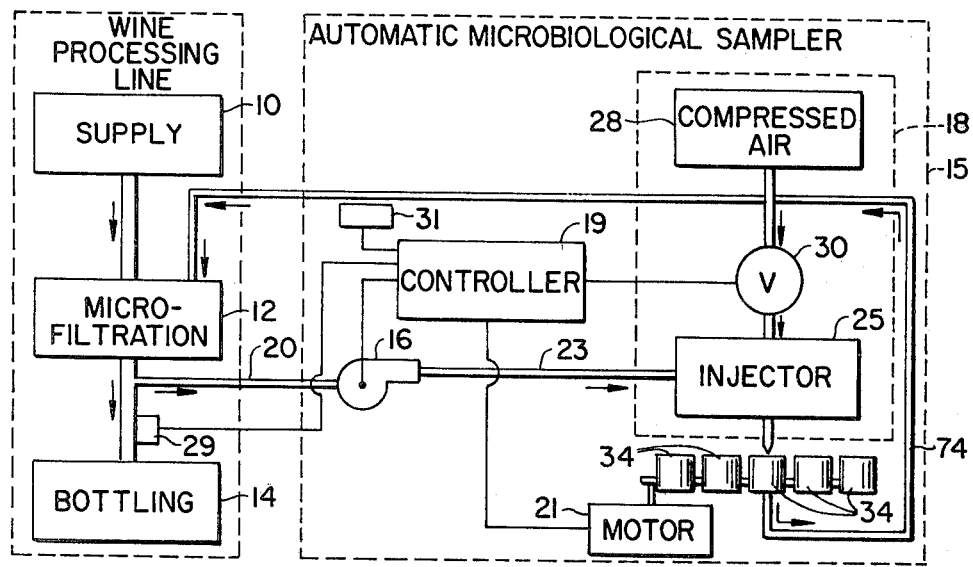
FIG._1.
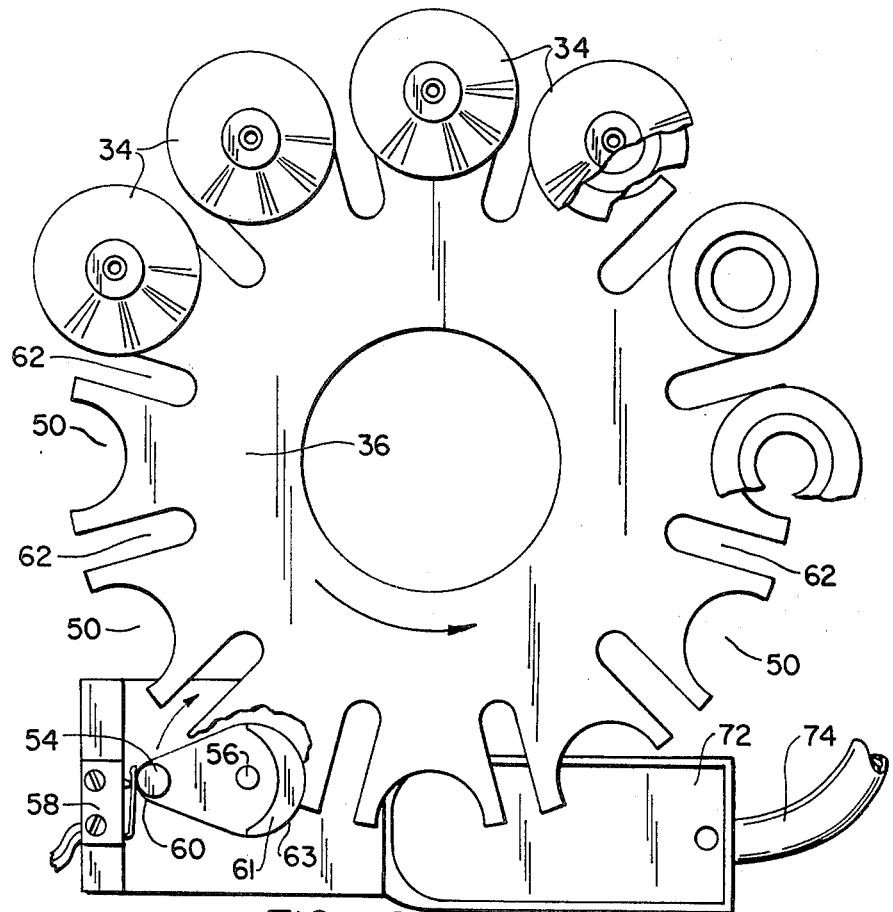
FIG._2.

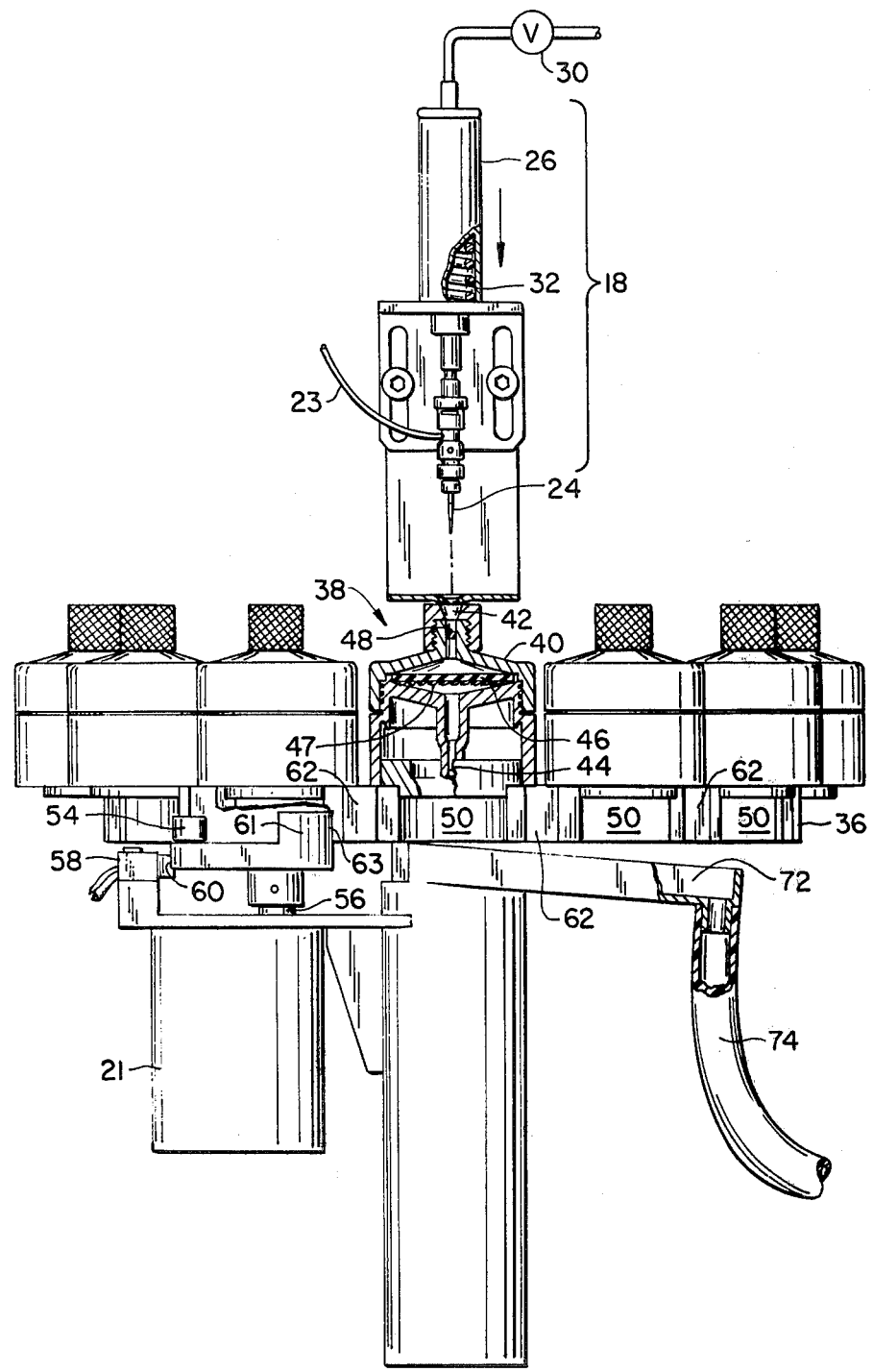
FIG._3.

METHOD AND APPARATUS FOR THE AUTOMATIC MICROBIOLOGICAL SAMPLING OF A LIQUID PRODUCT

BACKGROUND OF THE INVENTION

This invention relates to the processing of liquid products and to the detection of microorganisms which may be present in the liquid product during processing. More specifically, the invention relates to the continuous sampling of a liquid product during processing so that the detection of microorganisms in the sample may be readily correlated to a specific suspect batch of bottled product, which may then be isolated from uncontaminated batches of the bottled product.

In conventional liquid product processing lines in which the bottled product, for example any consumable product or drug, must be free of microorganisms, such as bacteria and yeast, microfiltration of microorganisms in the product flowing in the processing line occurs generally between the product supply station and the bottling station. The integrity of the microfiltration system is periodically examined by taking discrete random samples of the product which is flowing between the microfiltration system and the bottling station.

These liquid product samples are passed through sterile membranes which filter out microorganisms. The membranes are then introduced to a nutrient medium and incubated for a period of time. If the membrane has filtered out microorganisms the subsequent incubation of the membranes on the nutrient medium will result in a growth of microorganism colonies which are visible, either microscopically or to the naked eye.

The time required for the visual detection of microorganism colonies depends upon the particular microorganism and may vary from 24 to 96 hours. Detection of "micro" colonies may be possible within 18 hours by use of a microscope. In a modified but generally less accurate method, the detection of microorganisms can occur much faster by taking advantage of the enzyme activity of living cells. By treating or staining the membrane with a fluorescein-containing substance, free fluorescein will accumulate in living cells as a result of esterase activity, rendering the cells fluorescent when viewed under light of a specific wavelength. The detection of microorganisms in the sampled product in either of the above methods permits holding the bottled product for inspection.

More recently, continuous in-line sampling of the liquid product flowing in a processing line has been accomplished by diverting a portion of the liquid flowing between the microfiltration system and the bottling station through a container which houses a sterile membrane. A portion of the liquid product flowing to the bottling station is diverted through the membrane for a specific period of time, usually several hours. The diverted flow is then stopped, the container removed and the membrane placed in a nutrient medium where incubation will possibly result in the detection of microorganism colonies.

This more recent sampling method has several inherent disadvantages. In high speed bottling lines, such as are now common in the wine industry, the detection of microorganisms by such a method requires that large amounts of the finished bottled product be held for examination, since it is not possible to specifically isolate those bottles which may be contaminated with microorganisms. Additionally, since contamination of the liquid product frequently occurs when the supply tanks and the microfiltration systems are periodically changed, i.e., during periods when no liquid product is flowing to the bottling station, it is not possible to sample the liquid product during such periods.

SUMMARY OF THE INVENTION

This invention provides a method and apparatus for the automatic sampling of a liquid product flowing in a processing line whereby the subsequent detection of microorganisms in the sample product can be readily correlated to specific batches of the bottled product. The invention allows for sampling during periods when the supply tanks and microfiltration system are changed.

Generally speaking, the method involves directing a continuous stream of the flowing liquid product out of the processing line and collecting microorganisms from that stream for consecutive predetermined time intervals. All of the microorganisms which have been collected for each predetermined time interval constitute a group of microorganisms which are introduced to a nutrient medium and incubated to enhance the growth of microorganism colonies. The automatic collection of microorganisms from the stream for predetermined time intervals, the sorting of microorganisms into groups and the incubation of the collected and sorted microorganisms permit the correlation of microorganism detection in any one group to possible contamination of a specific batch of product which was bottled during the time interval when the suspect group of microorganisms was collected.

The automatic microbiological sampler comprises generally means for directing a continuous stream of liquid product, such as wine, away from the processing line at a point between the microfiltration system and the bottling station on the wine processing line, a plurality of microorganism collection devices, means for sequentially passing the stream of wine through each of the collection devices in turn, and means for controlling the time interval that the wine is passed through each of the collection devices.

The microorganism collection devices, each of which comprises generally a container having an inlet and an outlet, a sterile membrane fixed within the container and a diaphragm sealing the sterile membrane from the inlet, are arranged around the circumference of a horizontally oriented rotatable carousel. The rotatable carousel having the collection devices arranged around its outer circumference is incrementally rotated by a cam mechanism connected to a motor.

Disposed above the rotatable carousel and vertically aligned with the circumference of the carousel is a vertically movable wine injection means which is capable of engagement with the inlet of each of the collection devices, as the collection devices are incrementally advanced under the injection means. The wine injection means comprises a hollow probe which is vertically movable by a pneumatic cyclinder activated by a solenoid valve which allows compressed air to pass to the pneumatic cylinder. A spring raises the cylinder and probe when the solenoid valve is closed.

A conduit line interconnects the wine processing line and the hollow probe of the injection means.

Located in the conduit line between its point of connection to the wine processing line and the wine injection means is a positive displacement pump which directs a continuous stream of wine away from the wine processing line at a flow rate that is relatively constant and less than the high velocity flow rate in the processing line.

A controller, electrically coupled to the pump, the motor, and the solenoid valve, times the interval that wine passes through each of the collection devices, and controls the sequence of operation of the automatic microbiological sampler.

Means are also provided for automatically terminating sampling in response to the cessation of flow of the wine to the bottling station, for permitting sampling during periods when the supply tanks and microfiltration system are being changed and contamination is likely to occur, for returning the sampled stream back to the processing line so as to prevent wasting the wine, and for controlling the temperature of the sampler.

In the operation of the automatic microbological sampler, wine is flowing at a relatively high flow rate through the processing line from the supply, through the microfiltration system and to the bottling station. The inlet of one of the microorganism collection devices on the carousel is aligned directly below the wine injection means. The hollow probe of the injection means is in its withdrawn or uppermost position.

At the initiation of automatic sampling the controller signals the solenoid valve to open, thereby allowing compressed air to force the pneumatic cylinder and therewith the hollow probe through the inlet and the diaphragm of the first collection device. The controller then activates the postive displacement pump which directs a stream of wine away from the processing line and through the conduit line at a relatively constant flow rate. The stream is pumped through the conduit line and into the injection means and hollow probe where it passes into the container, through the sterile membrane and out the outlet.

The stream passes through the first sterile membrane for a predetermined time interval. At the end of this time interval, the controller stops the pump and deactivates the solenoid which closes the valve connecting the injection means with the compressed air source. The hollow probe is raised out of the inlet of the first collection device by the return spring. The controller next signals the motor to rotate the cam mechanism which incrementally rotates the carousel so that the next collection device is aligned directly under the injection means, thereby completing one cycle of automatic sampling.

After the stream of wine has passed through each of the collection devices for predetermined time intervals, the collection devices are removed from the carousel, the membranes are removed from the collection devices, nutrient medium is introduced to the membranes, and the membranes and nutrient medium are incubated for a specific time period during which microorganism colonies will become visible if the membrane filtered out any microorganisms. The collection devices may be chosen to filter out microorganisms larger than a predetermined size. Alternatively, the membrane after incubation may be subjected to staining which will disclose the presence of microorganisms in a much shorter time than required for visual inspection of microorganism colonies.

When the wine supply tanks and microfiltration system must be changed, as occurs periodically, the flow of wine to the bottling station is stopped and the sampler is switched out of its continuous automatic sampling mode. Thus, for example, after a new microfiltration system has been installed, wine can be passed directly to the sampler even though there is no flow to the bottling station, and the integrity of the new microfiltration system can be determined before large amounts of wine are bottled.

Since the automatic microbiological sampler passes a stream of wine at a relatively constant flow rate through a microorganism collection device for a predetermined time interval and since during the passage of that stream wine is also flowing into the bottling station, it is possible to correlate microorganisms on any one of the collection devices with a specific batch of bottled wine. Accordingly, less stock of bottled wine need be retained for later inspection. Furthermore, the continuous automatic sampling of the wine flowing in the processing line in the above manner permits rapid detection of any degradation in the microfiltration system thereby minimizing the amount of bottled product which may be contaminated.

The novel features which are believed to be characteristic of the invention, together with objects and advantages thereof, will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a block diagram of a wine processing line and the automatic microbiological sampler.

FIG. 2 is a top view of the rotatable carousel with several microorganism collection devices retained on its outer periphery.

FIG. 3 is a front view illustrating the wine injector the motor and cam means for rotating the carousel, and one of the microorganism collection devices in cross section.

DESCRIPTION OF THE PREFERRED EMBODIMENTS

Referring to FIG. 1, conventional wine processing lines include a wine supply 10, a microfiltration system 12, and a bottling station 14. As the wine flows at a relatively high rate through the processing line, the microfiltration system 12, which consists of a membrane of relatively small pore size, filters out microorganisms such as bacteria and yeast. The integrity of the membrane of the microfiltration system 12 in conventional wine processing lines must be inspected regularly to insure that no microorganisms reach the the bottled product.

If the membrane of the microfiltration system 12 has any tears or holes, even of a relatively small size, microorganisms may pass through the microfiltration system 12 and into the bottled product. Additionally, even if the membrane remains intact, in-line pressure surges in the wine flowing in the processing line may pass microorganisms through the membrane and ultimately into the bottled product.

The automatic microbiological sampler 15, which provides continuous in-line monitoring of the wine flowing in the wine processing line, comprises generally means, such as positive displacement pump 16 and conduit 20, for directing a stream of wine away from the wine processing line; a wine injection means 18 for injecting the stream of wine into microogranism collection devices 34; means, such as motor 21, for advancing the collection devices 34 into cooperation with the injection means 18; and a controller 19 for controlling the automatic sequence of operation.

The pump 16 is a positive displacement pump which is inter-connected by conduit 20 to a portion of the wine processing line between the microfiltration system 12 and the bottling station 14. The output side of the positive displacement pump 16 is connected by conduit 23 to the wine injection means 18. While any type of pump may be used, a positive displacement pump is preferred since such a pump operates at a constant flow rate and measures a pre-determined amount of wine through the pump in any given period of time. Additionally, the use of positive displacement pump 16 allows for selecting any desired flow rate for the stream and for measuring that selected flow rate. Since it is desired to maintain the relatively high flow rate in the wine processing line, the stream of wine which is directed out of the wine processing line by pump 16 flows at a relatively small flow rate, for example, 100 milliliters per minute.

The pump 16 and conduit 20 direct a stream of wine away from the wine processing line, through conduit 23 and into the injector 25 of wine injection means 18. The rate of flow of the stream of wine may be selected and measured by monitoring the operation of pump 16 because pump 16 is a positive displacement pump. Referring to FIG. 3, the wine injection means 18 comprises generally a hollow probe 24 fluidly connected to conduit 23, a pneumatic cylinder 26 operatively connected to the hollow probe 24, a solenoid valve 30, and compressed air source 28. The pneumatic cylinder 26 is fluidly connected to the compressed air source 28, and is activated by a solenoid valve 30 located between the pneumatic cylinder 26 and the compressed air source 28. A return spring 32 automatically returns or raises the pneumatic cylinder 26 and therewith the hollow probe 24 when the solenoid valve 30 closes so as to block air from the compressed air source 28.

The stream of wine which is thus directed away from the wine processing line by the pump 16 into conduit 23 and through hollow probe 24 of injector 25 passes in sequence through the plurality of microorganism collection devices 34. Referring to FIGS. 2 and 3, the microorganism collection devices 34 are retained on a horizontally-oriented rotatable carousel 36. The hollow probe 24 of injector 25 is vertically aligned generally with the outer periphery of rotatable carousel 36 so as to be specifically aligned with the inlet 42 of each of the microorganism collection devices 34 as the devices 34 rotate in turn beneath the hollow probe 24.

Referring to FIG. 3, a typical pre-sterilized microorganism collection device 38 is illustrated in cross section. The microorganism collection device 38 comprises generally a container 40 having an inlet 42 for the receipt of hollow probe 24, and an outlet 44; a sterile membrane 46 retained within the container 40 between inlet 42 and outlet 44; an absorbent pad 47 containing nutrient medium located beneath membrane 46; and a seal 48 for maintaining the sterility of membrane 46 and providing a seal between membrane 46 and inlet 42. Each of the microorganism collection devices 34 is retained on the outer periphery of the rotatable carousel 36 by residing within a semi-circular cutout 50 having a diameter less then the diameter of the container 40.

Referring to FIGS. 2 and 3, the means for advancing the microorganism collection devices 34 so as to be aligned directly under hollow probe 24 of injector 25 comprises generally the rotatable carousel 36, a motor 21, a cam 54 operatively connected to shaft 56 of motor 21, and a microswitch 58 engagable by outer portion 60 of cam 54. Disposed around the outer periphery of rotatable carousel 36 and located between the semi-circular cutouts 50 are radially oriented slots 62 engageable by cam 54 so that as shaft 56 rotates approximately 180 degrees, cam 54 engages one of the slots 62 so as to rotate carousel 36 an angular increment of rotation corresponding to the angular separation of two adjacent radially oriented slots 62. Also connected to shaft 56 and disposed 180° from cam 54 is rod 61 which extends partially upward into a cutout 50. The radial distance from the center of shaft 56 to the outer surface 63 of rod 61 is approximately equal to one-half the diameter of a semicircular cutout 50.

While the preferred means for advancing the microorganism collection devices 34 into alignment with the injector 25 is the above-described carousel 36, motor 21, and cam 54, numerous alternative advancing means, such as a moving conveyor system, are within the scope of the present invention.

Wine is returned to the wine processing line by tray 72 located beneath outlet 44 of the collection device 38 disposed vertically beneath hollow probe 24, and conduit 74 interconnecting tray 72 and a point on the processing line between microfiltration system 12 and wine supply 10. Thus as wine passes through each of the collection devices 34 in turn and out outlet 44 it falls into return tray 72, passes through conduit 74 and back to the wine processing line where it may again be filtered through the membrane in microfiltration system 12.

In order to inhibit the growth of microorganism colonies in the stream flowing in the automatic microbiological sampler and specifically within the membranes of the microorganism collection devices 34, the sampler is preferably retained within a refrigeration unit (not shown). Thus as microorganisms are collected by membrane 46, they are kept alive by nutrient medium contained on absorbent pad 47. The cooling of the sampler inhibits reproduction of the microorganisms collected until the membrane 46 is removed from the sampler. While this is the preferred method, it may be desireable to initiate incubation immediately. This is accomplished by heating the sampler to a controlled temperature.

The automatic sequential operation and control of the automatic microbiological sampler is provided by controller 19 which is electrically coupled to pump 16, solenoid valve 30, and motor 21. This electrical coupling is provided essentially by time delay relays (not shown). The microswitch 58 is part of an electrical circuit between the motor power supply (not shown) and motor 21. For safety reasons, a voltage drop between motor power supply (not shown) and microswitch 58 may be supplied by any conventional device. A time delay relay (not shown) coupled to controller 19 is part of a separate parallel circuit between motor power source (not shown) and motor 21. Controler 19 is also coupled to a transducer 29, preferably a flow sensor or pressure sensor, which senses the cessation of flow of wine to bottling station 14. In the event of the cessation of flow in the processing line, transducer 29 signals controller 19 to terminate sampling. A reset switch 31 coupled to controller 19 is also provided to permit manual override of the automatic sampler.

The invention as thus described can be better understood by considering the component parts in operation. Prior to the initation of the sampling of wine from the wine processing line, wine is flowing in the wine processing line from supply 10 through the membrane of microfiltration system 12 and into bottling station 14. The pump 16 is off so that no stream of wine is directed away from the processing line. The solenoid valve 30 is closed, thereby allowing spring 32 to retain hollow probe 24 in its uppermost position, as depicted in FIG. 3. One of the plurality of mircroorganism collection devices 34 is vertically aligned below hollow probe 24 and ready for the injection of wine. Surface 63 of rod 61 is contacting the inner wall of one of the cutouts 50, thereby locking carousel 36 from rotation.

At the initiation of the sampling process, controller 19 signals solenoid valve 30 to open, thereby allowing compressed air from source 28 to pass into pneumatic cylinder 26, and forcing cylinder 26 and therewith hollow probe 24 downward. As hollow probe 24 is forced downward by pneumatic cylinder 26, probe 24 enters inlet 42 of collection device 38 and punctures seal 48. Controller 19 next signals pump 16 to turn on, thereby directing a stream of wine from the wine processing line through conduit 20 to pump 16, into conduit 23 and probe 24. The stream flows at a relatively constant flow rate and at a flow rate less than the flow rate in the wine processing line. The wine passes through hollow probe 24 into container 40 and onto sterile membrane 46. In addition to sealing membrane 46 from inlet 42, seal 48 prevents the backflow of wine as the wine slowly passes through membrane 46 and absorbent pad 47.

The stream of wine directed away from the wine processing line through conduit 23 and probe 24 passes through membrane 46 for a predetermined time interval. In one embodiment this interval is approximately 20 minutes. If microorganisms are flowing between microfiltration system 12 and bottling station 14 during this time interval, some of those microorganisms will be collected on membrane 46 of collection device 38. After the wine has passed through membrane 46 it exits outlet 44 of collection device 38, passes into tray 72 and conduit 74 and is then returned back to the inlet side of microfiltration system 12 of the wine processing line.

At the termination of the predetermined time interval, controller 19 signals pump 16 to shut off, thereby stopping the flow of the stream of wine through conduit 20. Therefore, between such time intervals the stream of wine in conduit 20 is stopped by the action of controller 19 signaling pump 20 to shut off. Controller 19 then signals solenoid valve 30 to close, thereby shutting off the supply of compressed air from compressed air source 28 to pneumatic cylinder 26. The spring 32 then forces pneumatic cylinder 26 and therewith hollow probe 24 upward, thereby withdrawing hollow probe 24 from collection device 38.

The controller next signals motor 21 for a relatively brief instant so that power is applied to motor 21 for this brief instant of time. During this brief instant of time motor 21 drives cam 54 away from microswitch 58. The microswitch 58, which was previously in the open position because of the contact provided by portion 60 of cam 54, now closes so as to complete the circuit between the motor power source (not shown) and motor 21, thereby allowing the motor 21 to drive cam 54 in a clockwise direction. The controller 19 is now essentially inoperative with respect to motor 21 since power is supplied from motor power source (not shown) through an electrical circuit including the closed microswitch 58.

Rod 61 is rotated away from locking engagement with the inner wall of cutout 50 and rotating cam 54 now engages one of the slots 62 so that as cam 54 rotates it moves carousel 36 in a counter-clockwise direction. As cam 54 continues to rotate it moves first radially inward within slot 62 and then radially outward. As cam 54 continues to rotate in the clockwise direction it rotates carousel 36 counter-clockwise. After rotating cam 54 is no longer engaging slot 62, carousel 36 has been rotated a predetermined incremental amount. This incremental rotation of carousel 36 now aligns the next microorganism collection device directly under hollow probe 24 of injector 25. Since microswitch 58 continues to be closed, cam 54 continues to rotate in the clockwise direction but is no longer engaging slots 62 of rotatable carousel 36. When cam 54 has made approximately one complete revolution, portion 60 of cam 54 engages the microswitch 58 to thereby open the circuit between the motor 21 and the motor power source (not shown) so as to turn off motor 21. Once again rod 61 is engaged with the inner wall of the next cutout 50 thus locking carousel 36 from rotation. One complete cycle of operation of the microbiological sampler has thus been completed.

After all the microorganism collection devices 34 retained on carousel 36 have had wine passed through them for a predetermined time interval, they are removed from carousel 36 and the membranes 46 within them are introduced to a nutrient medium. The nutrient medium and membrane 46 of each of the collection devices 34 are incubated for a period of time until microorganism colonies are visible, either microscopically or to the naked eye. In one embodiment, as illustrated in FIGS. 2 and 3, twelve microorganism collection devices are retained on a rotatable carousel, and wine is flowed through each of the microorganism collection devices 34 for approximately 20 minutes. Accordingly, one carousel 36 would permit the automatic sampling of wine flowing in the wine processing line for a period of four hours.

If upon subsequent incubation of membrane 46 microorganism colonies are visible or if the above-described staining technique determines that microorganisms are present, this detection of microorganisms on one particular collection device permits the correlation of microorganisms detected during a predetermined time interval with a suspect batch of wine bottled during that same time interval. Since in the wine processing line, the wine which is bottled and packaged into cases is stamped with the time of bottling, it is thus possible to isolate particular suspect bottles and cases of wine which may then be separated from the uncontaminated bottled wine. Such a method thus permits the holding of only a relatively small amount of bottled product for subsequent inspection to determine if indeed microorganisms are present in that bottled product.

As should now be apparent, the method and apparatus of the present invention permits the automatic sampling of wine for the detection of microorganisms and the correlation of microorganisms detected during a predetermined time interval with a relatively small batch of wine bottled during that time interval. Fewer amounts of bottled wine need be held for inspection to determine if they are indeed contaminated with microorganisms. Additionally, the failure of the microfiltration system can be pinpointed to a specific instant by inspection of the membranes on the microorganism collection devices. Such rapid determination of the failure of the membrane in the microfiltration system thus prevents the continued processing of wine through a wine processing line having a damaged microfiltration system.

While the preferred embodiments of the present invention have been illustrated in detail, it should be apparent that modifications and adaptations of those embodiments will occur to those skilled in the art. However, it is to be expressly understood that such modifications and adaptations are within the sphere and scope of the present invention as set forth in the following claims.

What is claimed is:

1. A method of automatically sampling for microorganisms in a liquid product flowing in a liquid product processing line, the method comprising the steps of:
    directing a stream of liquid product away from the liquid product flowing in the processing line at a flow rate less than the flow rate in the processing line;
    collecting microorganisms from the stream for consecutive time intervals;
    sorting the microorganisms collected during said time intervals into groups, each of said groups corresponding to a respective time interval, such that the microorganisms in any of said groups are a generally representative sample of the microorganisms present in the liquid product flowing in the processing line during the respective time interval;
    incubating said microorganisms collected from the stream; and
    detecting said microorganisms collected from the stream.

2. The method accordingly to claim 1 including the step of redirecting said stream back into the liquid product flowing in the processing line after the mircroorganisms have been collected from said stream.

3. The method according to claim 1 including the step of measuring the rate of flow of said stream.

4. The method according to claim 1 including the step of stopping the flow of said stream between said consecutive time intervals.

5. The method according to claim 1 including the step of controlling the temperature of the collected microorganisms.

6. The method according to claim 5 wherein the step of controlling the temperature includes the step of cooling the collected microorganisms so as to inhibit the growth of microorganism colonies.

7. The method according to claim 1 including the step of predetermining the duration of each of said time intervals.

8. The method according to claim 1 wherein the step of collecting includes the step of filtering said stream for microorganisms larger than a predetermined size.

9. The method according to claim 8 wherein the step of sorting includes the step of introducing nutrient medium to said filtered microorganisms.

10. The method according to claim 1 including the steps of terminating flow of the stream in response to a cessation of flow in the processing line.

11. In a method of processing wine through a processing line of the type having a wine supply, a bottling station, a filter between the supply and bottling station for removing microorganisms in wine flowing from the supply to the bottling station, and a plurality of sterile membranes for collection of microorganisms present in representative samples of wine flowing between the filter and the bottling station, a method for automatically sampling the flowing wine for microorganisms so as to correlate mircroorganisms detected in a representative sample with microorganisms present in the bottled wine, the method comprising the steps of:
    directing a stream of wine away from the wine flowing in the processing line between the filter and the bottling station at a flow rate less than the rate of flow of wine between the filter and the bottling station;
    sequentially passing said stream through each of said sterile membranes for predetermined time intervals, whereby the subsequent detection of mircroorganisms on a membrane indicates the presence of microorganisms in wine bottled generally during the time interval when wine was passed through that membrane;
    incubating said membrane after having said stream pass therethrough for said predetermined time; and
    detecting said microorganisms collected on said membrane so that the presence of microorganisms in wine bottled generally during the time interval when wine was passed through said membrane is indicated.

12. The method according to claim 11 including the step of redirecting said stream of wine back to said processing line between the wine supply and the filter after said stream has passed through a membrane.

13. The method according to claim 11 including the step of stopping the flow of said stream between said time intervals.

14. The method according to claim 11 including the step of simultaneously controlling the temperature of the sterile membranes.

15. The method according to claim 14 wherein the step of controlling the temperature includes step of cooling the sterile membranes so as to inhibit the growth of microorganism colonies.

16. The method according to claim 11 including the step of measuring the rate of flow of said stream.

17. The method according to claim 11 wherein the step of directing a stream of wine away from the wine flowing in the processing line includes the step of maintaining the rate of flow of said stream relatively constant.

18. In apparatus for the automatic sampling for microorganisms in a liquid product flowing in a processing line, the improvement comprising:
    a plurality of microorganism collection filter devices;
    means for directing a stream of liquid product from said processing line;
    means for sequentially passing the stream through a respective microorganism collection filter device;
    means coupled with said sequential passing means for controlling the time interval during which the stream passes through its respective microorganism collection filter device;
    means for incubating said collected microorganisms; and
    means for detecting the presence of said incubated microorganisms.

19. Apparatus according to claim 18 wherein said directing means includes means for maintaining the flow rate of the stream relatively constant.

20. Apparatus according to claim 18 including means for measuring the flow rate of the stream.

21. Apparatus according to claim 18 wherein said controlling means is coupled with said directing means.

22. Apparatus according to claim 18 wherein said sequential passing means further comprises means for injecting the stream into said microorganism collection filter devices and means for advancing each of said microorganism collection filter devices into operative connection with said injection means at the end of a time interval.

23. Apparatus according to claim 22 wherein said stream injection means comprises a compressed air actuated hollow probe for perforating the seals of said microorganism collection filter devices.

24. Apparatus according to claim 22 wherein said advancing means comprises a rotatable carousel for retaining said collection devices in a generally circular arrangement and means for incrementally rotating said carousel so as to align the microorganism collection filter devices with said injection means.

25. Apparatus according to claim 18 including means for returning the stream to the processing line after the stream has passed through said microorganism collection filter devices.

26. Apparatus according to claim 18 including means adaptable with the processing line for sensing the cessation of flow of liquid product in the processing line, and means coupled with said sensing means for terminating the flow of the stream.

27. Apparatus according to claim 18 including cooling means for inhibiting growth of microorganism colonies in said microorganism collection filter devices.

28. Apparatus according to claim 18 wherein said controlling means includes means for varying the duration of each of the time intervals.

29. Apparatus according to claim 18 wherein each of said microorganism collection filter devices comprises a sterile membrane and a seal for sealing said sterile membrane from the outside environment.

30. An apparatus for automatically sampling wine for the detection of microorganisms, the apparatus comprising:
a plurality of microorganism collection devices, each of said devices further comprising a container having an inlet, an outlet, a sterile membrane between said inlet and said outlet for filtering microorganisms out of the wine, and a seal sealing said membrane from said inlet for maintaining the sterility of said membrane;
a carousel for retaining said collection devices generally on its outer periphery;
means for delivering the wine to said collection devices, said delivering means further comprising a pump for flowing the wine under pressure, means for injecting the wine into said collection devices, and conduit means interconnecting said pump and said injection means;
means operatively connected to said carousel for incrementally rotating said carousel so as to sequentially align the inlet of each of said collection devices with said injection means;
means coupled with said pump, said injection means, and said rotating means for controlling the duration of time that wine flows through each of said collection devices.

31. Apparatus according to claim 30 wherein said wine injection means further comprises a hollow probe in fluid communication with said conduit means and a movable cylinder operatively connected to said probe for moving said probe through the inlet and the seal of each of said collection devices.

32. Apparatus according to claim 30 wherein said rotating means further comprises a motor and cam means operatively interconnecting said motor and said carousel.

* * * * *